US 6,841,569 B2

(12) United States Patent
Choi et al.

(10) Patent No.: US 6,841,569 B2
(45) Date of Patent: Jan. 11, 2005

(54) CARBAMATES OF 2-HETEROCYCLIC-1,2-ETHANEDIOLS

(75) Inventors: Yong-Moon Choi, Towaco, NJ (US); Ki-Ho Lee, Daejon (KR)

(73) Assignee: SK Corporation, Fairfield, NJ (US)

( * ) Notice: Subject to any disclaimer, the term of this patent is extended or adjusted under 35 U.S.C. 154(b) by 26 days.

(21) Appl. No.: 10/177,041

(22) Filed: Jun. 21, 2002

(65) Prior Publication Data

US 2003/0078235 A1 Apr. 24, 2003

Related U.S. Application Data

(60) Provisional application No. 60/300,730, filed on Jun. 25, 2001.

(51) Int. Cl.⁷ .................... A61K 31/38; C07D 333/12

(52) U.S. Cl. ................ 514/438; 549/75; 549/76
(58) Field of Search ................. 549/75, 76; 514/438

(56) References Cited

U.S. PATENT DOCUMENTS

| 2,884,444 A | 4/1959 | Berger et al. |
| 2,937,119 A | 5/1960 | Berger et al. |
| 5,854,283 A | 12/1998 | Choi et al. |
| 6,274,590 B1 * | 8/2001 | Talley et al. ............ 514/277 |
| 6,414,013 B1 * | 7/2002 | Fancelli et al. .......... 514/438 |

* cited by examiner

*Primary Examiner*—Deborah C. Lambkin

(57) ABSTRACT

Carbamate compounds of 2-heteroaryl-1,2-ethanediol are described. The compounds are effective in the treatment of disorders of the central nervous system, especially as anti-convulsive or anti-epileptic agents.

14 Claims, No Drawings

CARBAMATES OF 2-HETEROCYCLIC-1,2-ETHANEDIOLS

This Application claims priority from U.S. Provisional Application 60/300,730 filed Jun. 25, 2001.

FIELD OF THE INVENTION

The invention relates to pharmaceutically useful compounds for the treatment of central nervous system disorders; particularly useful as anticonvulsants, antiepileptics, neuroprotective agents and muscle relaxants. More specifically, the invention relates to carbamates of 2-heterocyclic-1,2-ethanediols

BACKGROUND

Chiral or racemic carbamate compounds of aryl alkanols have been known to be useful as antiepileptics and as muscle relaxants. In U.S. Pat. No. 5,854,283, the optically pure forms of monocarbamate of halogenated 2-phenyl-1,2-ethanediol and dicarbamate of 2-phenyl-1,2-ethanediol have been found to be effective in the treatment of disorders of the central nervous system, especially as anti-convulsive or anti-epileptic agents.

It has been reported in Toxicol. and Appl. Pharm. 2, 397–402 (1960) that (2-phenyl-2-hydroxyethyl) oxocarboxamide is effective as an antiepileptic agent. Dicarbamates of 2-methyl-3-propyl-1,3-propanediol and their pharmacological effects have been described in J. Pharmacol. Exp. Ther., 104, 229 (1952).

In U.S. Pat. No. 2,884,444, dicarbamates of 2-phenyl-1,3-propanediol have been disclosed. Also, in U.S. Pat. No. 2,937,119 carbamates, such as isopropylmeprobamate have been disclosed.

Some of the carbamates described in the previous paragraphs are currently being used in the treatment of central nervous system disorders.

In accordance with the present invention there are provided carbamates of 2-heterocyclic-1,2-ethanediols, including pharmaceutical compositions containing them as the active ingredient and methods of using the pharmaceutical compositions in the treatment of diseases of the central nervous system.

SUMMARY OF THE INVENTION

The invention relates to compounds of the formula

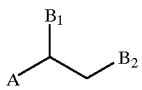

(I)

wherein A is a heterocyclic moiety optionally substituted by one or more substituents selected from the group consisting of alkyl, aryl, halogen, trihalomethyl, trihalomethoxy, trialkylsilyl, S(O)R, SO$_2$R, SO$_2$NRR', SO$_3$R, SR, NO$_2$, NRR', OR, CN, C(O)R, OC(O)R, NHC(O)R, CO$_2$R and CONRR', wherein R and R' are independently hydrogen, alkyl or aryl; B$_1$ and B$_2$ are independently hydroxy or OCONR$_1$R$_2$, provided that B$_1$ and B$_2$ are not simultaneously hydroxy, and R$_1$ and R$_2$ are independently selected from the group consisting of hydrogen, hydroxy, alkyl, alkoxy, alkylaryl, arylalkyl, aryl and aryloxy, and their enantiomers, as well as enantiomeric mixtures, and pharmaceutically acceptable salts thereof.

The compounds of formula I, their enantiomers, as well as enantiomeric mixtures, and pharmaceutically acceptable salts thereof are useful in the treatment of central nervous system diseases, particularly, as anticonvulsants, antiepileptics, neuroprotective agents and centrally acting muscle relaxants.

DETAILED DESCRIPTION OF THE INVENTION

The invention relates to compounds of the formula

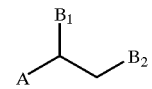

(I)

wherein A is a heterocyclic moiety optionally substituted by one or more substituents selected from the group consisting of alkyl, aryl, halogen, trihalomethyl, trihalomethoxy, trialkylsilyl, S(O)R, SO$_2$R, SO$_2$NRR', SO$_3$R, SR, NO$_2$, NRR', OR, CN, C(O)R, OC(O)R, NHC(O)R, CO$_2$R and CONRR', wherein R and R' are independently hydrogen, alkyl or aryl; B$_1$ and B$_2$ are independently hydroxy or OCONR$_1$R$_2$, provided that B$_1$ and B$_2$ are not simultaneously hydroxy,: and R$_1$ and R$_2$ are independently selected from the group consisting of hydrogen, hydroxy, alkyl, alkoxy, alkylaryl, arylalkyl, aryl and aryloxy, and their enantiomers, as well as enantiomeric mixtures, and pharmaceutically acceptable salts thereof.

A preferred group of compounds of the present invention are compounds of formula (I) wherein A is selected from the group consisting of

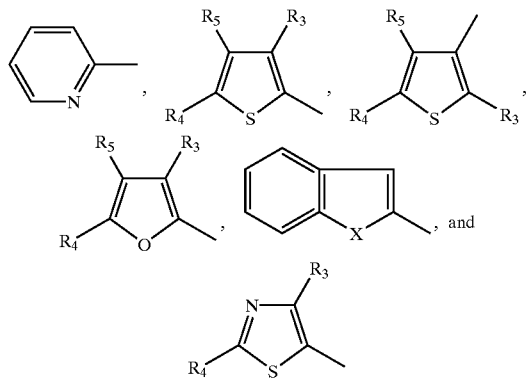

wherein R$_3$, R$_4$ and R$_5$, each independently, is selected from the group consisting of hydrogen, halogen, trihalomethyl, alkyl and aryl, and X is selected from sulfur, oxygen and nitrogen.

A more preferred compounds of according to the present invention are compounds of formula I wherein A is

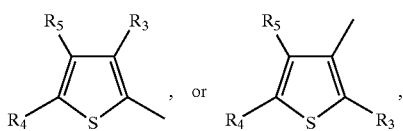

wherein R$_3$, R$_4$ and R$_5$ are as previously described.

Illustrative of the compounds of formula (I) are the following:

(±)-(2-(5-chloro-2-thienyl)-2-carbamoyloxyethyl) oxocarboxamide.

(+)-(2R)-(2-(5-chloro-2-thienyl)-2-carbamoyloxyethyl)oxocarboxamide;

(−)-(2S)-(2-(5-chloro-2-thienyl)-2-carbamoyloxyethyl)oxocarboxamide;

(2-(5-trifluoromethyl-2-thienyl)-2-carbamoyloxyethyl)oxocarboxamide.

(2-(5-bromo-2-thienyl)-2-carbamoyloxyethyl)oxocarboxamide.

(2-(2-thienyl)-2-carbamoyloxyethyl)oxocarboxamide;

N-methyl-(2-(5-chloro-2-thienyl)-2-N-methylcarbamoyloxyethyl)oxocarboxamide;

(2-(5-phenyl-2-thienyl)-2-carbamoyloxyethyl)oxocarboxamide;

(2-(3,4,5-trichloro-2-thienyl)-2-carbamoyloxyethyl)oxocarboxamide;

(2-(5-methyl-2-thienyl)-2-carbamoyloxyethyl)oxocarboxamide;

(2-(2,5-dichloro-3-thienyl)-2-carbamoyloxyethyl)oxocarboxamide;

(2-(2-benzothienyl)-2-carbamoyloxyethyl)oxocarboxamide; and (2-(5-tert-butyl-2-thienyl)-2-carbamoyloxyethyl)oxocarboxamide.

As used herein, the term "lower alkyl" is to be understood to mean a straight-or branched-chain alkyl group of 1 to 6 carbon atoms, such as methyl, ethyl, isopropyl, butyl, pentyl, hexyl, and the like with methyl being preferred. The term "halogen" is to be understood to mean all of the halogens, that is, bromine, chlorine, fluorine and iodine; with bromine and chlorine being preferred. The term "lower alkoxy" is to be understood to mean a lower alkyl ether group in which the lower alkyl moiety is as described above, such as methoxy, ethoxy, propoxy, butoxy and the like with methoxy being preferred.

Additional examples of the heterocyclic groups represented by A in formula (I) include the following:

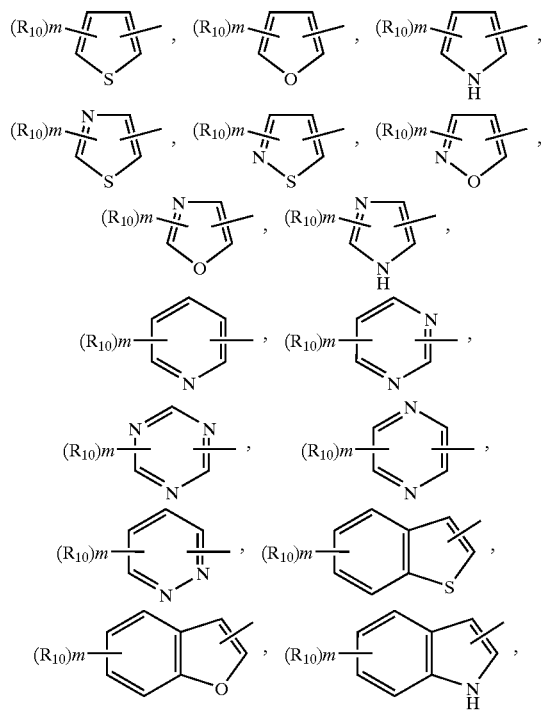

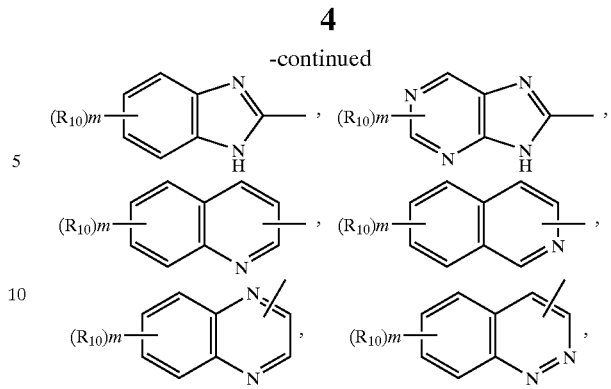

and the like, wherein each $R_{10}$ is the same or different and represents a substituent selected from the group consisting of hydrogen, alkyl, aryl, halogen, trihalomethyl, trihalomethoxy, trialkylsilyl, $S(O)R$, $SO_2R$, $SO_2NRR'$, $SO_3R$, $SR$, $NO_2$, $NRR'$, $OR$, $CN$, $C(O)R$, $OC(O)R$, $NHC(O)R$, $CO_2R$ and $CONRR'$, m is 1–3; and R and R' are independently selected from the group consisting of hydrogen, alkyl and aryl.

The starting materials for the compounds of the present invention are represented by the general formula

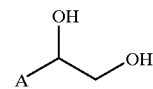

wherein A is a heterocyclic ring as defined above. These 2-heterocyclic-1,2-ethanediols are known per se or can be conveniently prepared by a dihydroxylation reaction of the corresponding styrenic compound. Optically active diols can be prepared according to the procedure given in K. Sharpless et. al., J. Org. Chem 56:4585~8(1991).

The compounds of formula I above wherein only one of $B_1$ and $B_2$ is a carbamate group can be prepared by the synthetic method described in Scheme 1, a detailed description of which follows. The 2-heterocyclic-1,2-ethanediol starting material is reacted with dimethyl carbonate in the presence of catalytic amount of sodium methoxide. The by-product that forms is removed by vacuum distillation and the residual product dried in vacuo. The crude reaction product is subsequently dissolved in a lower alkanol, such as methanol, and an excess amount of an amine is added to the reaction solution at room temperature to provide two regioisomeric forms of a monocarbamate of 2-heterocyclic-1-2-ethanediol.

Reaction Scheme 1

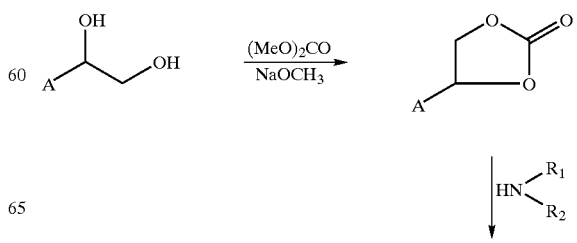

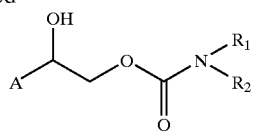

The compounds of the present invention wherein both of $B_1$ and $B_2$ are carbamate groups and the carbamate groups are the same may be prepared directly from the 2-heterocyclic-1-2-ethanediol starting material according to the reaction of Reaction Scheme 2 as described below. The 2-heterocyclic-1-2-ethanediol is dissolved in dichloromethane and is treated with about 2 equivalents of carbonyl diimidazole. The resulting mixture is stirred until the starting material is not observed by thin layer chromatography analysis, and the mixture is then treated with excess amounts of amine ($R_1R_2NH$ wherein $R_1$ and $R_2$ are as defined above). It takes more than 24 hours to complete the reaction. After a routine aqueous wash, the crude reaction product is purified by flash column chromatography or recrystallization to provide the desired compound of formula I.

Reaction Scheme 2

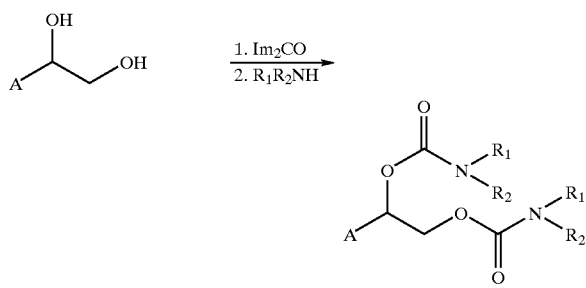

The compounds of the present invention wherein both of $B_1$ and $B_2$ are carbamate groups and the carbamate groups are different may be prepared from the corresponding monocarbamate compound represented by formula I in accordance with Reaction Scheme 3. The 2-heterocyclic-1-2-ethanediol monocarbamate is treated with about 1 equivalent of carbonyl diimidazole. The resulting mixture is stirred until the starting material is not observed by thin layer chromatography analysis, after which the mixture is treated with an excess amount of amine ($R_1R_2NH$ wherein $R_1$ and $R_2$ are as defined above, but are different in at least one particular from those of the starting material).

Reaction Scheme 3

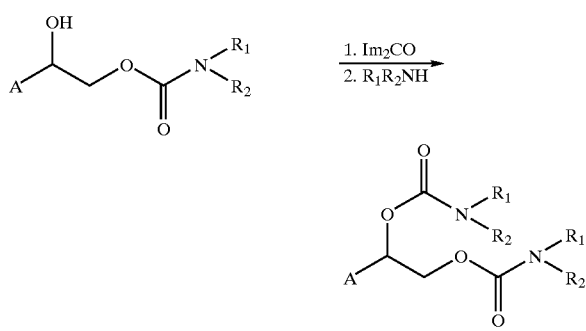

Exemplary of the 2-heterocyclic-1,2-ethanediols starting materials in accordance with the present invention are the following:

1-(2-thienyl)-1,2-ethanediol;
1-(5-chloro-2-thienyl)-1,2-ethanediol;
1-(5-phenyl-2-thienyl)-1,2-ethanediol;
1-(3,4,5-trichloro-2-thienyl)-1,2-ethanediol;
1-(2-benzothienyl)-1,2-ethanediol;
1-(5-cyano-2-thienyl)-1,2-ethanediol;
1-(2-furanyl)-1,2-ethanediol; and the like.

The compounds of the invention contain chiral centers. The compounds of formula (I) contain an asymmetric carbon atom at the position, which is the aliphatic carbon adjacent to the heteroaromatic ring. The scope of the invention includes pure enantiomeric forms and enantiomeric mixtures, wherein one of the enantiomer predominates in the compound of formula (I). Preferably, one of the enantiomers predominates to the extent of about 90% or greater, and most preferably, about 98% or greater.

The compounds of formula (I) of the invention, which have basic amine functional group like as amino, pyridyl or imidazolyl can form salts with inorganic and organic acids including, for example, hydrochloric acid, hydrobromic acid, methanesulfonic acid, and the like. These salts are prepared following procedures well known to those skilled in the art.

In utilizing the compounds of the invention for the treatment of diseases of the central nervous system, particularly the treatment of convulsions, epilepsy, neurogenic pain, stroke and muscle spasm, it is preferred to administer the compounds orally. Moreover, since the compounds of formula (I) are absorbed orally, it will not be necessary to resort to parenteral administration. For oral administration, the compounds of formula (I) are preferably combined with a pharmaceutical carrier. The ratio of the carrier to a compound of formula (I) is not critical to achieve the desired effects on the central nervous system of the host requiring such treatment, and can vary considerably, depending on whether the composition is to be filled into capsules or formed into tablets. In tableting, it is usually desirable to employ at least as much pharmaceutical carrier as the pharmaceutically active ingredients. Various pharmaceutical carriers or mixtures thereof can be used. Suitable carriers, for example, comprise mixtures of lactose, dibasic calcium phosphate and corn starch. Other pharmaceutically acceptable ingredients can be further added, including lubricants such as magnesium stearate.

The compounds of formula (I) can be formulated, using conventional inert pharmaceutical adjuvant materials, into dosage forms that are suitable for oral or parenteral administration. Such dosage forms include tablets, suspensions, solutions, and the like. Furthermore, the compounds of the invention can be administered in the form of hard or soft capsules. Examples of suitable inert adjuvant materials that can be used in formulating the compounds of formula (I) into oral and parenteral dosage forms will be immediately apparent to persons skilled in the art. These adjuvant materials include, for example, water, gelatin, lactose, starch, magnesium stearate, talc, vegetable oils, gums, polyalkylene glycols, and the like. Moreover, preservatives, stabilizers, wetting agents, emulsifying agents, salts for altering osmotic pressure, buffers, and the like, can be incorporated, if desired, into such formulations.

The therapeutic use of the compounds of formula I as anticonvulsants has been established by the "Maximal ElectroShock (MES)" test, which is a well-established pharmacological screening method for anticonvulsants against partial seizures, and the results are presented in Table I. The procedure employed in the MES test for anticonvulsants is as follows. The dosing solutions of the compounds to be tested were prepared in saline. The subjects, namely, mice (ICR strain), were dosed i.p. After the designated number of hours, maximal electroshock was induced in mice via corneal electrodes using IITC Life Science model 11A Shocker at 50 mA-60 Hz for 0.2 second. Anticonvulsant activity is demonstrated by the elimination of hindlimb tonic extension upon inducing maximal electroshock. Median efficacy dose ($ED_{50}$) levels were determined using three different dose levels with at least 6 mice in each group. Compounds with smaller $ED_{50}$ value are more potent as anticonvulsants.

The "Pentylenetetrazol (PTZ)" test for anticonvulsant activity was also carried out. Compounds that antagonize the effects of subcutaneous PTZ-induced seizures are known to elevate the threshold for seizures, hence are generally useful in preventing such seizures. The procedure employed in the PTZ test for anticonvulsants follows. The compound dosing solutions were prepared in saline, and mice (ICR strain), were dosed i.p. After the designated number of hours, each animal was injected subcutaneously with 100 mg/kg of PTZ($CD_{97}$ dose) and observed for up to 30 minutes for the presence or absence of threshold clonic seizures of 2 second duration or longer. Median efficacy dose ($ED_{50}$) levels were determined using three different dose levels with 8 mice in each group. The compounds with a smaller $ED_{50}$ value are more potent as anticonvulsants.

Test results obtained with the compounds of formula I of the invention are set forth in Table I.

TABLE I

| Compound Of Example | MES $ED_{50}$ (mg/Kg) | PTZ $ED_{50}$ (mg/Kg) | Hour |
|---|---|---|---|
| 4 | 16.9 | 31.3 | 2 |
| 5 | 8.4 | 47.2 | 2 |
| 6 | 36.9 | 42.7 | 2 |
| 7 | 37.4 | — | 1 |
| 14 | 12.6 | — | 1 |
| 17 | 14.9 | 50 | 1 |
| 18 | 19.6 | — | 1 |

The data presented in Table 1 demonstrate that the compounds of formula (I) of the invention possess anticonvulsant activity by preventing the occurrence of electroshock seizures, and also protecting the host against convulsions produced by pentylenetetrazole.

The amount of a compound of formula (I) which is present in any of the above-described dosage forms is variable. In the systemic treatment of CNS diseases with a active amount of compounds of the formula (I), the dosage is typically from about 0.02 mg to about 250 mg/kg/day (0.001~12.5 g/day in a typical human weighing 50 kg) in single or divided doses, regardless of the route of administration. A more preferred dosage range is from about 0.15 mg/kg/day to about 250 mg/kg/day. Of course, depending upon the exact compound and the exact nature of the individual illness, doses outside this range may be prescribed by the attending physician.

The examples, which follow further, illustrate the invention. All parts are by weight and all temperatures are in degrees centigrade, unless otherwise mentioned.

Moreover, unless otherwise stated, NMR spectra were obtained at 200 Mhz, melting points are uncorrected, and optical rotations were measured with a automatic polarimeter.

EXAMPLE 1

Preparation of (±)-(2-(2-thienyl)-2-carbamoyloxyethyl)oxocarboxamide.

1,1'-Carbonyldiimidazole (4.5 g) was added to a solution of 1-(2-thienyl)-1,2-ethanediol (1.0 g 6.9 mmol) in dichloromethane (15 mL) at 5°. The reaction mixture was allowed to come to room temperature with stirring over one hour. Ten ml of an aqueous solution of ammonium hydroxide (28% NH3 in water) was added at 5°. The reaction mixture was stirred for 1 hour at room temperature, extracted with ethyl acetate, washed with 0.5N aqueous hydrochloric acid, saturated sodium bicarbonate and brine. The extracts were dried over sodium sulfate, filtered, concentrated and purified by recrystallization from dichloromethane to yield the title compound as a white solid (1.2 g, yield 74%). M.p. 158–159° (from dichloromethane). $[\alpha]_D^{24'}$=0' (c=0.005, methanol).

EXAMPLE 2

Preparation of (+)-(2R)-(2-(2-thienyl)-2-carbamoyloxyethyl)oxocarboxamide.

The title compound was prepared in accordance with the procedure of Example 1, except that (+)-(1R)-1-(2-thienyl)-1,2-ethanediol (M.p. 48~50° from carbon tetrachloride) was used instead of (±)-1-(2-thienyl)-1,1-ethandiol. M.p. 183–184° (from dichloromethane). $[\alpha]_D^{24'}$=+63 (c=0.005, methanol).

EXAMPLE 3

Preparation of (−)-(2S)-(2-(2-thienyl)-2-carbamoyloxyethyl)oxocarboxamide

The title compound was prepared in accordance with the procedure of Example 1, except that (−)-(1S)-1-(2-thienyl)-1,2-ethanediol (M.p. 48~50° from carbon tetrachloride) was used instead of (±)-1-(2-thienyl)-1,1-ethandiol. M.p. 184–185° (from dichloromethane). $[\alpha]_D^{24'}$=−56 (c=0.005, methanol).

EXAMPLE 4

Preparation of (±)-(2-(5-chloro-2-thienyl)-2-carbamoyloxyethyl)oxocarboxamide.

The title compound was prepared in accordance with the procedure of Example 1, except that (±)-1-(5-chloro-2-thienyl)-1,2-ethanediol (M.p. 50~51° from carbon tetrachloride) was used instead of (±)-1-(2-thienyl)-1,1-ethandiol. M.p. 154~156° (from dichloromethane). $[\alpha]_D^{24'}$=0' (c=0.005, methanol).

EXAMPLE 5

Preparation of (+)-(2R)-(2-(5-chloro-2-thienyl)-2-carbamoyloxyethyl)oxocarboxamide.

The title compound was prepared in accordance with the procedure of Example 1, except that (+)-(1R)-1-(5-chloro-2-thienyl)-1,2-ethanediol (M.p. 78~80° from carbon tetrachloride) was used instead of (±)-1-(2-thienyl)-1,1-ethandiol. M.p. 185–186° (from dichloromethane). $[\alpha]_D^{24'}$=+55 (c=0.005, methanol).

EXAMPLE 6

Preparation of (−)(2S)-(2-(5-chloro-2-thienyl)-2-carbamoyloxyethyl)oxocarboxamide.

The title compound was prepared in accordance with the procedure of Example 1, except that (−)-(1S)-1-(5-chloro-2-thienyl)-1,2-ethanediol (M.p. 77~78° from carbon tetrachloride) was used instead of (±)-1-(2-thienyl)-1,1-ethandiol. M.p. 185–186° (from dichloromethane). $[\alpha]_D^{24'}$=−52 (c=0.005, methanol).

EXAMPLE 7

Preparation of N-methyl-(2-(5-chloro-2-thienyl)-2-(N-methylcarbamoyloxyethyl)oxocarboxamide The title compound was prepared in accordance with the procedure of Example 1, except that methylamine was used instead of ammonium hydroxide. M.p. 104–106° (from hexane:ethyl acetate=5:1).

EXAMPLE 8

Preparation of (2-(5-phenyl-2-thienyl)-2-carbamoyloxyethyl)oxocarboxamide.

The title compound was prepared in accordance with the procedure of Example 1, except that 1-(5-chloro-2-thienyl)-1,2-ethanediol (M.p. 77~78° from carbon tetrachloride) was used instead of (±)-1-(2-thienyl)-1,1-ethandiol. M.p. 202–203° (from methanol).

EXAMPLE 9

Preparation of (2-(3,4,5-trichloro-2-thienyl)-2-carbomoyloxyethyl)oxocarboxamide The title compound was prepared in accordance with the procedure of Example 1 utilizing 1-(3,4,5-trichloro-2-thienyl)-1,2-ethanediol as the starting material. M.p. 193–197° (from dichloromethane).

EXAMPLE 10

Preparation of (2-(5-methyl-2-thienyl)-2-carbomoyloxyethyl)oxocarboxamide

The title compound was prepared in accordance with the procedure of Example 1 utilizing 1-(5-methyl-2-thienyl)-1,2-ethanediol as the starting material. M.p. 172–173° (from dichloromethane).

EXAMPLE 11

Preparation of (2-(2,5-dichloro-3-thienyl)-2-carbomoyloxyethyl)oxocarboxamide

The title compound was prepared in accordance with the procedure of Example 1 utilizing 1-(2,5-dichloro-3-thienyl)-1,2-ethanediol as the starting material. M.p. 137–138° (from ether).

EXAMPLE 12

Preparation of (2-(3-trichloro-2-thienyl)-2-carbomoyloxyethyl)oxocarboxamide

The title compound was prepared in accordance with the procedure of Example 1 utilizing 1-(3-chloro-2-thienyl)-1,2-ethanediol as the starting material. M.p. 153–155° (from dichloromethane).

EXAMPLE 13

Preparation of (2-(2-benzothienyl)-2-carbomoyloxyethyl)oxocarboxamide

The title compound was prepared in accordance with the procedure of Example 1 utilizing 1-(2-benzothienyl)-1,2-ethanediol as the starting material. M.p. 195° (from dichloromethane).

EXAMPLE 14

Preparation of (2-(5-trifluoromethyl-2-thienyl)-2-carbomoyloxyethyl)oxocarboxamide The title compound was prepared in accordance with the procedure of Example 1 utilizing 1-(5-trifluoromethyl-2-thienyl)-1,2-ethanediol as the starting material. M.p. 159–160° (from dichloromethane).

EXAMPLE 15

Preparation of (2-(5-tert-butyl-2-thienyl)-2-carbomoyloxyethyl)oxocarboxamide

The title compound was prepared in accordance with the procedure of Example 1 utilizing 1-(5-tert-butyl -2-thienyl)-1,2-ethanediol as the starting material. M.p. 132–155° (from carbon tetrachloride).

EXAMPLE 16

Preparation of (2-(5-cyano-2-thienyl)-2-carbomoyloxyethyl)oxocarboxamide

The title compound was prepared in accordance with the procedure of Example 1 utilizing 1-(5-cyano-2-thienyl)-1,2-ethanediol as the starting material. M.p. 149–151° (from dichloromethane).

EXAMPLE 17

Preparation of (±)-(2-(5-bromo-2-thienyl)-2-carbamoyloxyethyl)oxocarboxamide.

N-bromosuccinimide (1.79 g) was added in portions to a solution of (±)-(2-(2-thienyl)-2-carbamoyloxyethyl)oxocarboxamide (2.2 g 9.5 mmol) in 40 ml of a 1:1 mixture of chloroform and acetic acid. The resulting suspension was stirred for 24 hours. The reaction mixture was then diluted with an equal volume of water and the separated organic layer was recovered, and sequentially washed with potassium hydroxide solution and water. The extracts were dried over sodium sulfate, filtered, concentrated and purified by recrystallization from dichloromethane to yield the title compound as a white solid (2.2 g). M.p. 160–161° (from dichloromethane).

EXAMPLE 18

Preparation of (+)-(2R)-(2-(5-bromo-2-thienyl)-2-carbamoyloxyethyl)oxocarboxamide.

The title compound was prepared in accordance with the procedure of Example 17, utilizing (+)-(2R)-(2-(2-thienyl)-2-carbamoyloxyethyl)oxocarboxamide as the starting material. M.p. 181–182° (from dichloromethane). $[\alpha]_D^{24'}$=+46' (c=0.005, methanol).

EXAMPLE 19

Preparation of (−)-(2S)-(2-(5-bromo-2-thienyl)-2-carbamoyloxyethyl)oxocarboxamide.

The title compound was prepared in accordance with the procedure of Example 17, except that the starting material was (−)-(2S)-(2-(2-thienyl)-2-carbamoyloxyethyl)oxocarboxamide instead of (±)-(2-(2-thienyl)-2-carbamoyloxyethyl)oxocarboxamide. M.p. 181–182° (from dichloromethane). $[\alpha]_D^{24'}$=−46' (c=0.005, methanol).

EXAMPLE 20

Preparation of (2-(5-nitro-2-thienyl)-2-carbamoyloxyethyl)oxocarboxamide.

In 4 ml of acetic anhydride there was suspended (2-(2-thienyl)-2-carbamoyloxyethyl)oxocarboxamide (0.50 g) and the resulting mixture was cooled to 0°. A mixture of nitric acid (60% in water 0.37 g) in 4 ml of acetic acid was added dropwise and the mixture was stirred at room temperature for 1.5 hours, poured into 100 ml of ice water, extracted with ethyl acetate and washed with saturated brine. The extracts were dried over sodium sulfate, filtered, concentrated and purified by recrystallization from ether to yield the title compound as a yellow solid (0.07 g, yield 12%). M.p. 145–1847 (from ether).

EXAMPLE 21

Preparation of (2-(2-thienyl)-2-hydroxyethyl) oxocarboxamide.

1,1'-Carbonyldiimidazole (1.13 g) was added to a solution of 1-(2-thienyl)-1,2-ethanediol (1.0 g) in 20 ml of dichloromethane at 5°. The reaction mixture was allowed to warm to room temperature, stirred for one hour and then concentrated in vacuo to yield 1-(2-thienyl)-1,2-ethanediol carbonate (1.07 g, 90.7% yield) as a colorless oil after chromatographic purification. The product was dissolved in 20 ml of tetrahydrofuran and 2 g of ammonium hydroxide (equivalent to 28% ammonia in water) was added thereto at 0°. The reaction mixture was slowly warmed to room temperature and was stirred thereafter for a further hour and then concentrated in vacuo to yield (2-(2-thienyl)-2-hydroxyethyl)oxocarboxamide (0.30 g, yield 25%) as a white solid after chromatographic purification. M.p. 71–73° (from dichloromethane).

EXAMPLE 22

Preparation of (2-(5-chloro-2-thienyl)-2-hydroxyethyl) oxocarboxamide.

The title compound was prepared in accordance with the procedure of Example 21, utilizing 1-(5-chloro-2-thienyl)-1,2-ethanediol as the starting material. M.p. 68–72° (from benzene).

EXAMPLE 23

Preparation of (2-(5-chloro-2-thienyl)-2-carbamoyloxy) ethan-1-ol

Imidazole (0.45 g) was added to a solution of 1(5-chloro-2-thienyl)-1,2-ethanediol (1.0 g, 5.6 mmol) and tert-butyldimethylsilyl chloride (0.80 g) in N,N-dimethylformamide (5 ml) at 5°. The reaction mixture was allowed to come to room temperature and stirred 1 hour, extracted with ethyl acetate, washed with 0.5N aqueous hydrochloric acid, saturated sodium bicarbonate and brine. The extracts were dried over sodium sulfate, filtered, concentrated in vacuo. 1-tert-butyldimethylsilyloxy-2-(5-chloro-2-thienyl)ethan-1-ol (1.14 g) was obtained as a colorless oil after a chromatographic purification. 1,1'-Carbonyldiimidazole (0.95 g) was added to a solution of the foregoing alcohol (1.14 g 3.9 mmol) in dichloromethane (20 mL) at 5°. The reaction mixture was allowed to come to room temperature and stirred 1 hour. Ammonium hydroxide (equivalent to 28% ammonia in water, 10 ml) was added at 5°. The reaction mixture was stirred for 1 hour at room temperature, extracted with ethyl acetate, washed with 0.5N aqueous hydrochloric acid, saturated sodium bicarbonate and brine. The extracts were dried over sodium sulfate, filtered, concentrated in vacuo. 1-tert-butyldimethylsilyloxy-2-(5-chloro-2-thienyl)-2-carbamoyloxyethane (0.47 g) was obtained as a colorless oil after a chromatographic purification.

Tetrabutylammonium fluoride (1.0M solution in tetrahydrofuran 2 ml) was added to a solution of the carboxamide formed above (0.47 g 1.6 mmol) in tetrahydrofuran (10 mL) at 5°. The reaction mixture was stirred 1 hour, extracted with ethyl acetate, washed with 0.5N aqueous hydrochloric acid, saturated sodium bicarbonate and brine. The extracts were dried over sodium sulfate, filtered, concentrated in vacuo. (2-(5-chloro-2-thienyl)-2-carbamoyloxy)ethan-1-ol (0.14 g) was obtained as a white solid after a chromatographic purification. M.p. 117–120' C (from dichloromethane).

EXAMPLE 24

Preparation of (2-(2-pyridyl)-2-carbamoyloxyethyl) oxocarboxamide.

The title compound was prepared in accordance with the procedure of Example 1 utilizing 1-(2-pyridyl)-1,2-ethanediol as the starting material in place of 1-(2-thienyl)-1,2-ethanediol. M.p. 173–174' C (from dichloromethane).

EXAMPLE 25

Preparation of (2-(2-pyridyl)-2-hydroxyethyl) oxocarboxamide

The title compound was prepared in accordance with the procedure of Example 21 utilizing 1-(2-pyridyl)-1,2-ethanediol as the starting material. M.p. 116–120° (from dichloromethane).

EXAMPLE 26

Preparation of (2-(2-pyridyl)-2-carbamoyloxy)ethan-1-ol

The title compound was prepared in accordance with the procedure of Example 23 utilizing 1-(2-pyridyl)-1,2-ethanediol as the starting material. M.p. 123–124° (from dichloromethane).

EXAMPLE 27

Preparation of N-methyl-(2-(2-pyridyl)-2-(N-methylcarbamoyloxyethyl)oxocarboxamide The title compound was prepared in accordance with the procedure of Example 1 utilizing methylamine in place of ammonium hydroxide. M.p. 114–115° (from chloroform/ether).

EXAMPLE 28

Preparation of (2-(2-furanyl)-2-carbamoyloxyethyl) oxocarboxamide

The title compound was prepared in accordance with the procedure of Example 1 utilizing 1-(2-furanyl)-1,2-ethanediol as the starting material. M.p. 155–560° (from dichloromethane).

EXAMPLE 29

Preparation of (2-(4-methyl-5-thiazolyl)-2-carbamoyloxyethyl)oxocarboxamide.

The title compound was prepared in accordance with the procedure of Example 1 utilizing 1-(4-Methyl-5-thiazolyl)-1,2-ethanediol as the starting material. M.p. 166–168' C (from dichloromethane).

EXAMPLE 30

Preparation of (2-(2-indolyl)-2-carbamoyloxyethyl) oxocarboxamide.

The title compound was prepared in accordance with the procedure of Example 1 utilizing 1-(2-Indolyl)-1,2-ethanediol as the starting material. M.p. 145–146° (from diethyl ether).

EXAMPLE 31

Preparation of (2-(5-trimethylsilyl-2-thienyl)-2-carbamoyloxyethyl)oxocarboxamide.

The title compound was prepared in accordance with the procedure of Example 1 utilizing 1-(5-trimethylsilyl-2-thienyl)-1,2-ethanediol as the starting material. M.p. 138–140' C (from dichloromethane).

What is claimed is:

1. A compound represented by the formula:

(I)

wherein A is a heterocyclic moiety selected from those represented by the formulae

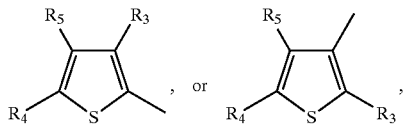

, or optionally substituted by one or more substituents selected from the group consisting of alkyl, aryl, halogen, trihalomethyl, trihalomethoxy, trialkylsilyl, S(O)R, $SO_2R$, $SO_2NRR'$, $SO_3R$, SR, $NO_2$, NRR', OR, CN, C(O)R, OC(O)R, NHC(O)R, $CO_2R$ and CONRR', wherein R and R' are independently hydrogen, alkyl or aryl; $B_1$ and $B_2$ are independently hydroxy or $OCONR_1R_2$, provided that $B_1$ and $B_2$ are not simultaneously hydroxy,: and $R_1$ and $R_2$ are independently selected from the group consisting of hydrogen, hydroxy, alkyl, alkoxy, alkylaryl, arylalkyl, aryl and aryloxy, and each of $R_3$, $R_4$ and $R_5$ is independently selected from the group consisting of hydrogen, halogen, trihalomethyl, alkyl and aryl, and their enantiomers, enantiomeric mixtures thereof, and pharmaceutically acceptable salts thereof.

2. A compound in accordance with claim 1, wherein said compound is a pure enantiomer or an enantiomeric mixture wherein one enantiomer predominates.

3. A compound in accordance with claim 1, wherein $B_1$ and $B_2$ are $OCONH_2$.

4. A compound in accordance with claim 1, wherein only one of $B_1$ and $B_2$ is $OCONH_2$.

5. A compound in accordance with claim 1, wherein said compound is (±)-(2-(5-chloro-2-thienyl)-2-carbamoyloxyethyl) oxocarboxamide.

6. A compound in accordance with claim 1, wherein said compound is (±)-(2R)-(2-(5-chloro-2-thienyl)-2-carbamoyloxyethyl) oxocarboxamide.

7. A compound in accordance with claim 1, wherein said compound is (−)-(2S)-(2-(5-chloro-2-thienyl)-2-carbamoyloxyethyl) oxocarboxamide.

8. A compound in accordance with claim 1, wherein said compound is (2-(5-trifluoromethyl-2-thienyl)-2-carbamoyloxyethyl) oxocarboxamide.

9. A compound in accordance with claim 1, wherein said compound is (2-(5-bromo-2-thienyl)-2-carbamoyloxyethyl) oxocarboxamide.

10. A pharmaceutical composition comprising an effective amount of a compound of in accordance with claim 1 for treating disorders of the central nervous system.

11. A pharmaceutical composition in accordance with claim 10, wherein the central nervous systems disorder being treated is selected from the group consisting of convulsions, epilepsy, stroke, neurogenic pain and muscle spasm.

12. A pharmaceutical composition in accordance with claim 10, wherein said compound is a pure enantiomer or an enantiomeric mixture wherein one enantiomer predominates.

13. A method for the treatment of a central nervous system disorder which comprises administering to a host requiring such treatment an effective amount of a compound in accordance with claim 1.

14. A method in accordance with claim 13, wherein said compound is a pure enantiomer or an enantiomeric mixture wherein one enantiomer predominates.

* * * * *